United States Patent [19]

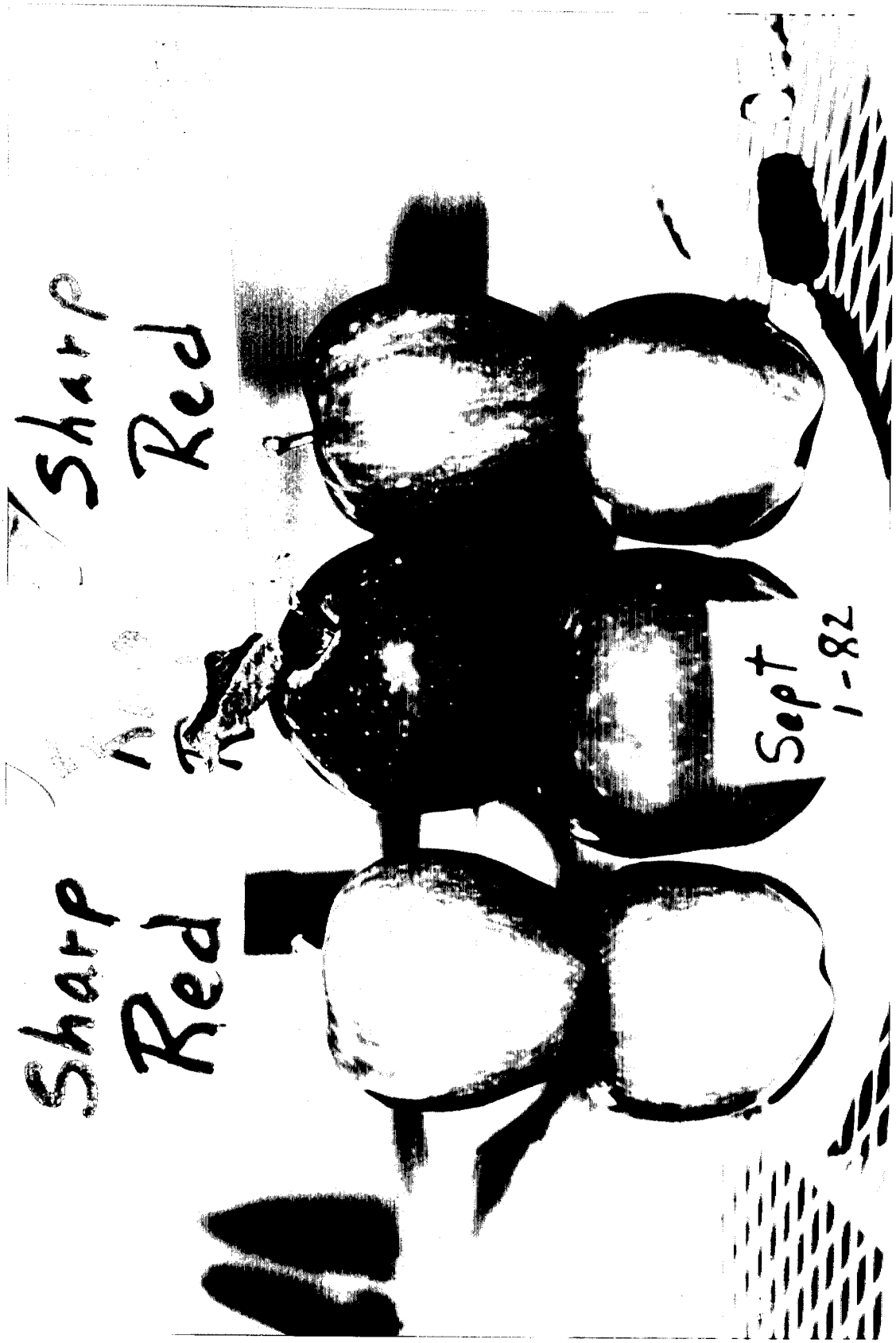
Sharp Red
Sharp Red
Sept 1-82

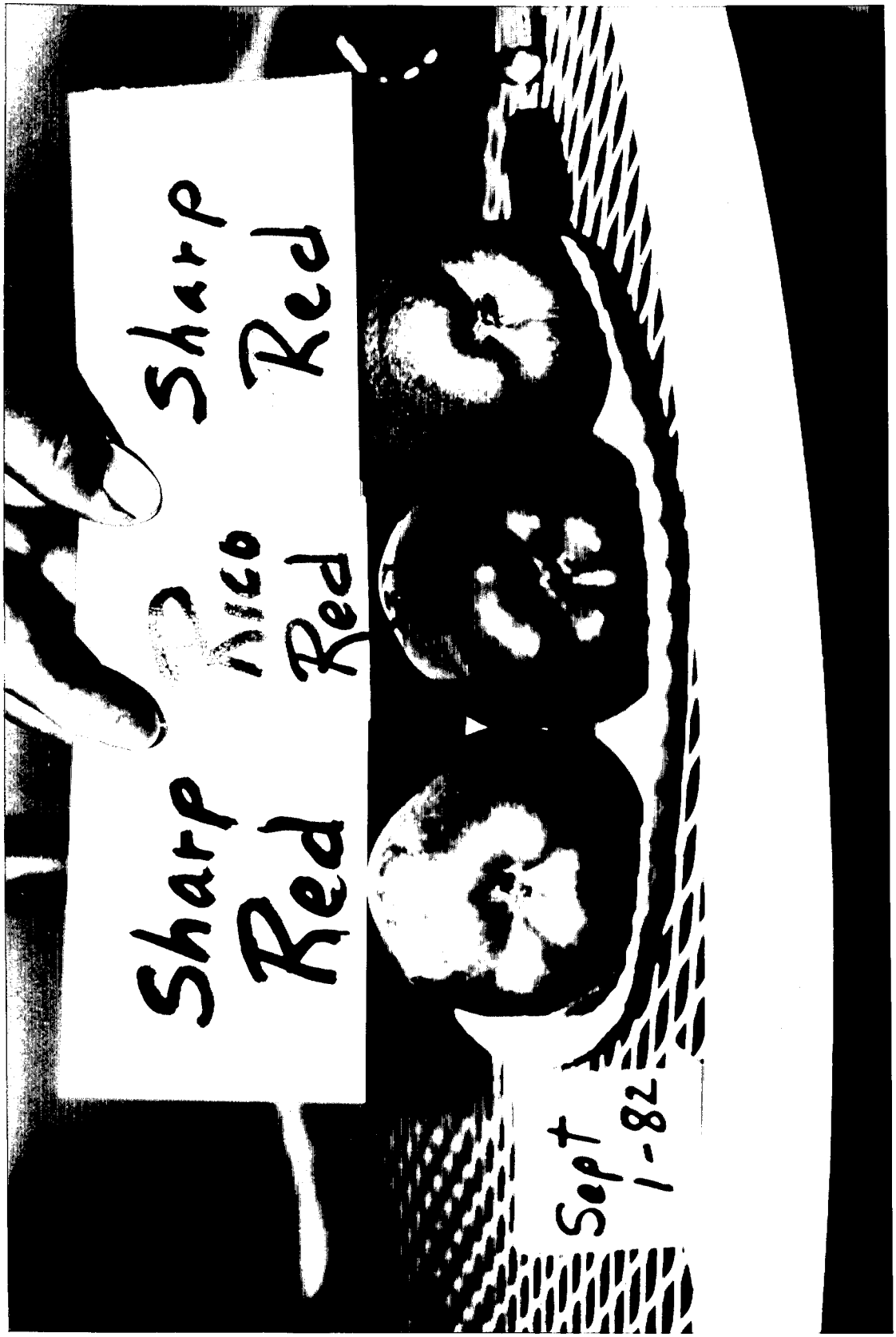
Sharp Red
Nico Red
Sharp Red
Sept 1-82

Gonzalez

[11] Patent Number: Plant 5,569

[45] Date of Patent: Oct. 8, 1985

[54] APPLE TREE 'RICO RED'

[75] Inventor: Richard Gonzalez, Royal City, Wash.

[73] Assignees: Donald K. Merkeley; Walter A. Topinka; Floyd F. Myrick, all of Seattle, Wash. ; part interest to each

[21] Appl. No.: 495,689

[22] Filed: May 18, 1983

[51] Int. Cl.[4] ..... A01H 5/00

[52] U.S. Cl. ..... Plt./35

[58] Field of Search ..... Plt./35

[56] References Cited

U.S. PATENT DOCUMENTS

P.P. 90 4/1934 Shotwell ..... Plt./35

*Primary Examiner*—James R. Feyrer

*Attorney, Agent, or Firm*—Christensen, O'Connor, Johnson & Kindness

[57] ABSTRACT

Anatomically and morphologically similar to its parent, Sharp Red Delicious, this new variety produces earlier coloring and maturing apples than those of its parent tree.

2 Drawing Figures

BACKGROUND

A nonspur type red delicious apple tree, this new and distinct cultivar originated as a single limb mutation in the lower whorl of branches of a central leader tree in the MTM Orchards east of Royal City, Wash. Reproduced by budding in those orchards through successive generations, this new variety of tree exhibits the bark, foliage, blossoming, bearing, spur and growth characteristics of its red delicious parent, a well-known, distinct variety produced and marketed by Van Well Nursery, Inc., of Wenatchee, Wash., under the name "Sharp Red"; but it differs from its parent in the fruit produced.

The earlier coloration and maturity of its fruit, even under vigorous conditions, makes this cultivar genetically new and unique. It has exhibited the ability to set a crop in the third or fourth leaf without plant growth regulator use. Its fruit size, color and quality are second to none.

DRAWINGS

FIG. 1 is a photographic side view and FIG. 2 a calyx end view of apples, those in the middle (labelled "Rico") being of the new variety and those on opposite sides thereof, for purposes of comparison, being of the Sharp red delicious variety.

DETAILED DESCRIPTION

The new tree, upon visual examination, reveals the morphological and anatomical characteristics of its parent, referred to above. However, its production of early season, highly colored fruit, sufficiently mature for the late summer and early fall markets give this new variety major economic importance in the orchard industry.

In more specific terms, fruit of the new variety is described as follows:

Fruit:

*Maturity when described.*—Mature from tree. Round in cross section and elongated. Large, dense with a L/D ratio of 0.93–0.95.

Skin: Smooth, waxy, with prominent lenticels. Moderately heavy with little chlorophyll (green). Red color (5R 4/12) develops early and remains bright (i.e. does not fade).

*Color: Strong yellowish green (2.5 Gr 5/9) early in the season, turning to a red stripe (5R 4/12) on green background 85–90 days from bloom, and a solid red on red stripe approximately 95 days post bloom (for example, on 8/15/81).

*Color hues from Nickerson Color Fan, American Horticultural Council, Arnold Arboretum, Jamaica Plain 30, Massachusetts.

Calyx: Lobed (usually 5), forming prominent basin, basin ¼ to ⅜ inches deep and 178 inches wide. Sepals at maturity small, obscure, yellowish-green in color. Closed calyx.

Stamens: In single whorl, persistent.

Flesh: White, clean, with vascular bundles obscure.

Seed: Amber to brown (5YR 4/5) in color with rounded distal end and sharp embryo end. Number varies from 2 to 8.

Seed cavities: Ovals in shape.

Use: Dessert, processing (juice).

Keeping quality: Very good, 120 days in cold storage.

With the new variety identified as "Rico Red", additional identification is made by comparing its fruit in terms of chemical and physical characteristics with that of its parent as follows, referenced to mature fruit:

MATURITY COMPARISON: "SHARP RED DELICIOUS" vs "RICO RED DELICIOUS" (as of 8-20-81)

| Fruit | Pressure | | Soluble Solids | | Starch[1] Rating | | Ethylene[2] | | % Surface Color | |
|---|---|---|---|---|---|---|---|---|---|---|
| No. | SR* | RR* | SR | RR | SR | RR | SR | RR | SR | RR |
| 1 | 18 | 18 | 9.8 | 10.7 | 1 | 1.5 | .15 | .22 | 85 | 100 |
| 2 | 18.8 | 20 | 9.4 | 11.0 | 1 | 2.0 | .10 | .24 | 90 | 100 |
| 3 | 20 | 18.5 | 9.8 | 10.2 | 1 | 2.0 | .15 | .20 | 85 | 95+ |
| 4 | 21 | 19 | 10.0 | 10.4 | 1 | 2.0 | .18 | .24 | 100 | 100 |
| 5 | 19 | 19 | 9.8 | 10.5 | 1 | 2.0 | .18 | .24 | 80 | 100 |
| 6 | 19.5 | 20 | 9.0 | 10.8 | 1 | 1 | .10 | .28 | 80 | 100 |
| 7 | 19.5 | 20 | 9.4 | 10.8 | 1 | 1.5 | .10 | .27 | 85 | 90 |
| Means | 19.4 | 19.2 | 9.5 | 10.6 | 1 | 1.7 | .14 | .24 | 86 | 97.8 |

SR = "Sharp Red Delicious"

RR = "Rico Red Delicious"

[1]Starch in a tangential cross-section was stained in a IKI solution and the distribution of starch rated as: (1) Starch present into the core area. (2) Starch had disappeared from the central core area. (3) Starch not present inside the vascular bundles. (4) Starch present in outer ¼ of apple. (5) Starch completely hydrolized.

[2]Ethylene was measured by placing a 200–250 gram fruit in a one quart sealed mason jar and held at 70–72° F. for one hour. A sample of the internal gas was removed and injected into a "Snoopy" ethylene detector connected to a Rus-Trac recorder. Calibration gases of .9 and 9 ppm were used as standards.

Further identification is made by comparing its fruit in terms of time of coloration with those of its parent and of other well-known Red Delicious cultivars, as follows:

| Cultivar | Date 1 | Date 2 | Date 3 |
|---|---|---|---|
| Delicious | 8/12/83 | 9/28/83 | 10/11/83 |
| Shotwell | 8/12/83 | 9/25/83 | 10/01/83 |
| Sharp Red | 8/06/83 | 9/09/83 | 9/28/83 |

-continued

| Cultivar | Date 1 | Date 2 | Date 3 |
|---|---|---|---|
| Rico Red | 8/06/83 | 8/25/83 | 9/08/83 |

Date 1 = First true red color
Date 2 = 60% of the fruit surface covered with deep red color
Date 3 = 90% of fruit would grade Washington Extra Fancy

I claim:

1. A new and distinct variety of apple tree similar in its anatomical and morphological characteristics to the parent tree "Sharp" Red Delicious, but distinguishable therefrom in the earlier coloration and maturity of its fruit, even under vigorous conditions, substantially as shown and described.

* * * * *

UNITED STATES PATENT AND TRADEMARK OFFICE

CERTIFICATE OF CORRECTION

PATENT NO. : Plant 5,569

DATED : October 8, 1985

INVENTOR(S) : Richard Gonzalez

It is certified that error appears in the above-identified patent and that said Letters Patent is hereby corrected as shown below:

Column 2, line 9, "178" should be —1/2—

Column 2, line 17, "Ovals" should be —Oval—

Signed and Sealed this

*Twelfth* Day of *August 1986*

[SEAL]

*Attest:*

DONALD J. QUIGG

*Attesting Officer*

*Commissioner of Patents and Trademarks*